US012697374B2

(12) United States Patent　　　(10) Patent No.:　US 12,697,374 B2
Herman et al.　　　　　　　　　　(45) Date of Patent:　　　Aug. 4, 2026

(54) USE OF CLOSTRIDIUM HISTOLYTICUM PROTEASE MIXTURE IN PROMOTING WOUND HEALING

(71) Applicant: SMITH & NEPHEW, INC., Memphis, TN (US)

(72) Inventors: Ira Herman, Boston, MA (US); Vincent Ronfard, Keller, TX (US); Lei Shi, Mansfield, TX (US)

(73) Assignee: SMITH & NEPHEW, INC.

( * ) Notice: Subject to any disclaimer, the term of this patent is extended or adjusted under 35 U.S.C. 154(b) by 0 days.

(21) Appl. No.: 18/581,040

(22) Filed: Feb. 19, 2024

(65) Prior Publication Data

US 2024/0261377 A1　　　Aug. 8, 2024

Related U.S. Application Data

(63) Continuation of application No. 15/534,547, filed as application No. PCT/US2015/065024 on Dec. 10, 2015, now Pat. No. 11,938,173.

(60) Provisional application No. 62/091,313, filed on Dec. 12, 2014.

(51) Int. Cl.
| | |
|---|---|
| *A61K 38/48* | (2006.01) |
| *A61K 9/00* | (2006.01) |
| *A61K 9/06* | (2006.01) |
| *A61K 9/70* | (2006.01) |
| *A61K 35/74* | (2015.01) |
| *A61K 45/06* | (2006.01) |

(52) U.S. Cl.
CPC ........ *A61K 38/4886* (2013.01); *A61K 9/0014* (2013.01); *A61K 9/06* (2013.01); *A61K 9/7007* (2013.01); *A61K 35/74* (2013.01); *A61K 38/48* (2013.01); *A61K 45/06* (2013.01); *C12Y 304/24003* (2013.01)

(58) Field of Classification Search
CPC .... A61K 38/4886; A61K 9/0014; A61K 9/06; A61K 9/7007; A61K 35/74; A61K 38/48; A61K 45/06; C12Y 304/24003; A61P 17/02
See application file for complete search history.

(56) References Cited

U.S. PATENT DOCUMENTS

| | | | |
|---|---|---|---|
| 3,705,083 | A | 12/1972 | Chiulli et al. |
| 3,821,364 | A | 6/1974 | Chiulli et al. |
| 5,718,897 | A | 2/1998 | Herman |
| 5,851,522 | A | 12/1998 | Herman |
| 6,548,556 | B2 | 4/2003 | Hobson et al. |
| 7,785,584 | B2 | 8/2010 | Jones et al. |

(Continued)

OTHER PUBLICATIONS

Ramundo et al. "Collagenase for Enzymatic Debridement" JWOCN Nov./Dec. 2009 (Year: 2009).*

(Continued)

*Primary Examiner* — Tracy Vivlemore
*Assistant Examiner* — Lauren K Van Buren
(74) *Attorney, Agent, or Firm* — Norton Rose Fulbright US LLP

(57) ABSTRACT

Provided are methods for repairing a wound or inducing the proliferative phase of a wound comprising administering a composition comprising a protease mixture comprising collagenases and a neutral protease to the wound in an amount effective for repair of wound tissue or for inducing the proliferative phase in the wound.

20 Claims, 2 Drawing Sheets

(56)                    References Cited

U.S. PATENT DOCUMENTS

| | | | |
|---|---|---|---|
| 8,357,655 | B2 | 1/2013 | Herman |
| 8,663,617 | B2 | 3/2014 | Herman |
| 9,694,100 | B2 | 7/2017 | Shi et al. |
| 10,058,596 | B2 | 8/2018 | Hanson |
| 2007/0128685 | A1 | 6/2007 | Faudoa et al. |
| 2009/0010869 | A9* | 1/2009 | Trumbore ............ A61K 9/0014 |
| | | | 424/94.1 |
| 2013/0287759 | A1* | 10/2013 | Munoz ............... A61K 38/4886 |
| | | | 435/219 |
| 2016/0008293 | A1 | 1/2016 | Shi et al. |

OTHER PUBLICATIONS

Das et al. "Novel mechanisms of Collagenase Santyl Ointment (CSO) in wound and resolutions of wound inflammation" Scientific Report (Year: 2017).*
Shi et al. "Collagenase Santyl Ointment, A Selective Agent for Wound Debridement" JWOCN Nov./Dec. 2009 (Year: 2009).*
Huang et al. "Ulceration and Delayed Healing Following Pressure Loading in Hyperglycemic Rats with an Immature Dermal Collagen Fiber Network" Wounds, 2010, 22(9); 237-244. (Year: 2010).*
Merriam Webster Definition of the word "wound" (Year: 2025).*
Saggini et al. "Extracorporeal shock wave therapy: an emerging treatment modality for retracting scars on the hands" Ultrasound in Med & Biol., vol. 42, No. 1, pp. 185-195, 2016. (Year: 2016).*
Merriam Webster Definition of Wound (Year: 2025).*
ClinicalTrials.gov [Internet]. Bethesda (MD): National Library of Medicine (US). Identifier NCT00651820, Effect of Collagenase on Healing and Scarring: Apr. 3, 2008 [Accessed on Aug. 7, 2018]: [16 pages] Available from: https://clinicaltrials.gov/ct2/show/NCT00651820.
Collagenase SANTYL Ointment [prescription information], Healthpoint, Ltd., Fort Worth, Texas; 2013.
Collagenase Santyl Ointment Brochure by Healthpoint (Year: 2013).
Herman, I., "Stimulation of Human Keratinocyte Migration and Proliferation in Vitro: Insights into the Cellular Responses to Injury and Wound Healing," Wounds: A Compendium of Clinical Research and Practice, 8(2), pp. 33-41. (1996).
International Search Report and Written Opinion Issued in Corresponding International Patent Application No. PCT/US2015/065024, mailed Apr. 3, 2016.
Postlehwaite, et al., "Chemotactic Attraction of Human Fibroblasts to Type I, II, and III Collagens and Collagen-Derived Peptides," *Proceeding of the National Academy of Sciences of the United States of America*, 75(2), pp. 871-875. (1978).
Radice, et al. "Clostridial Collagenase Releases Bioactive Fragments from Extracellular Matrix Models", *Journal of Burn Care & Rehabilitation*, 20(4), pp. 282-291. (1999).
Swezey et al. "Wound Source" Article, https://www.woundsource.com (Year: 2013).
Tallis, et al., "Clinical and Economic Assessment of Diabetic Foot Ulcer Debridement with Collagenase: Results of a Randomized Controlled Study," Clinical Therapeutics, 35(11), pp. 1805-1820. (2013).

* cited by examiner

Cells per well

Wound healing grade (a.u.)

USE OF CLOSTRIDIUM HISTOLYTICUM PROTEASE MIXTURE IN PROMOTING WOUND HEALING

CROSS-REFERENCE TO RELATED APPLICATION

This application is a national phase application under 35 U.S.C. § 371 of International Application No. PCT/US2015/065024, filed Dec. 10, 2015, which claims the benefit of U.S. Provisional Application No. 62/091,313, filed Dec. 12, 2014. The contents of the referenced application are incorporated into the present application by reference.

BACKGROUND OF THE INVENTION

A. Field of the Invention

The present invention relates generally to the field of biology. More particularly, it relates to methods for treating wounds with a protease mixture produced by *Clostridium histolyticum*. The mixture includes collagenases and a neutral protease. The collagenases include collagenase ColG and collagenase ColH.

B. Description of the Related Art

Wounds are cuts, tears, burns, breaks, or other damage to living tissue. Wound healing is done in stages. One stage of wound healing includes debridement. Debridement is the medical removal of dead, damaged, or infected tissue to improve the healing potential of the remaining healthy tissue. Removal may be surgical, mechanical, chemical, or autolytic (self-digestion). Autolytic debridement involves the use of the body's own enzymes and moisture to re-hydrate, soften and finally liquefy hard eschar and slough. Enzymatic debridement employs chemical enzymes that degrade proteinous materials in necrotic tissue. Mechanical and surgical debridement both use instruments or physical tools for the mechanical removal of necrotic tissue from the wound.

An example of enzymatic debridement is the use of Collagenase SANTYL® Ointment, which is an FDA-approved ointment prescribed for the removal of dead tissues from wounds. The SANTYL® Ointment, which is described in U.S. Pat. Nos. 3,705,083 and 3,821,364 (both of which are incorporated herein by reference), includes as its active ingredient a protease mixture derived from the fermentation by *Clostridium histolyticum*. The mixture includes unseparated collagenase in that collagenases and other non-specific proteases (e.g., a neutral protease) are present in the Ointment. The Ointment possesses the ability to digest collagen in necrotic tissue, thereby debriding the wound.

Once a wound has been debrided, it can then be treated with wound healing agents to promote wound repair. Importantly, wound debridement and wound repair are vastly different stages in the overall wound healing process. During the wound repair stage, cells begin to grow and rebuild missing and damaged tissues. Small blood vessels develop to deliver a blood supply to the wound. Skin cells then migrate, and scabs form within hours of the initial wound. These skin and epithelial cells can cover a properly closed surgical incision within 48 hours. In an open wound, the creation of granulation tissue takes longer.

Examples of wound repair can be found in U.S. Pat. No. 5,851,522 and in Herman I M, Stimulation of Human Keratinocyte Migration and Proliferation In Vitro: Insights into the Cellular Responses to Injury and Wound Healing, *WOUNDS: A Compendium of Clinical Research and Practice,* 1996, Volume 8, No. 2, Pages 33-41, both of which are incorporated herein by reference. U.S. Pat. No. 5,851,522 discloses a purified form of collagenase (i.e., Clostridiopeptidase A collagenase (EC 3.4.24.3), obtained by fermentation of *Clostridium histolyticum*) that was purified to be substantially free from other proteinases. Similarly, Herman (1996) discusses the use of purified *Clostridium* collagenase for wound healing.

While purified collagenase has been shown to promote wound repair, other types of active ingredients continue to be needed in today's society. By way of example, the proliferation of diabetes has resulted in an increase in diabetic ulcers, which are particularly known to be difficult wounds to repair. Having various types of wound repair agents available can be helpful in managing the debilitating health care implications and costs associated with wounds.

SUMMARY OF THE INVENTION

A solution to the lack of available wound repair agents has been discovered. In particular, it was discovered that a protease mixture produced by *Clostridium histolyticum* has the ability to promote wound healing. The mixture, which includes collagenase and a neutral protease, has been shown to promote adult human keratinocyte proliferation in a wound (see Example 1). In a particularly, preferred embodiment, the mixture is the active ingredient used in the aforementioned SANTYL® Ointment. Without wishing to be bound by theory, it is believed that the combination of collagenases (ColG and ColH) and a neutral protease promotes wound healing in wounds that have previously been debrided by releasing native peptides having wound healing functions from extracellular matrices present in the wound. In one aspect, there is disclosed a method for repairing a wound comprising administering a composition comprising a protease mixture produced from *Clostridium histolyticum* that includes collagenase(s) and a neutral protease to the wound in an amount effective for repair of wound tissue.

Further aspects relate to a method for inducing the proliferative phase of a wound comprising administering a composition comprising a protease mixture produced from *Clostridium histolyticum* that includes collagenases and a neutral protease to the wound in an amount effective for the induction of the proliferative phase in the wound. In some embodiments, the method is for promoting or inducing the angiogenesis aspect of the proliferative phase. Alternatively, or in conjunction, the method may also be for promoting or inducing other aspects of the proliferative phase described herein.

In another aspect, there is disclosed a method for repairing a wound or inducing the proliferative phase of a wound, the method comprising administering a composition comprising a protease mixture comprising collagenases and a neutral protease to the wound in an amount effective for repair of wound tissue or for inducing the proliferative phase in the wound.

Administration of an "amount" of a composition to a subject refers to administration of "an amount effective" to achieve the desired therapeutic result, including without limitation treatment of the subject.

In some embodiments, protease mixture includes, in addition to a neutral protease, additional non-collagenase proteases. The amount of the neutral protease in the protease mixture can be 0.1 wt. % to 10 wt. %, or 1 wt. % to 5 wt. %, or 2 wt. % to 4 wt. % of the mixture. In other instances, the protease mixture of the present invention does not include or contains limited amounts (e.g., less than 1 wt. % or less than 0.5 wt. % or less than 0.1 wt. % or less than 0.01 wt. %) of clostripain.

In some embodiments, the composition is comprised in a wound dressing. In some embodiments, the wound dressing is a patch, wrap, or bandage. In some embodiments, the composition is comprised in a spray. In some embodiments, the composition is a liquid, salve, dissolvable gel-forming film, cream, powder, film, semi-solid, etc. In some embodiments, the composition administered to the wound is Collagenase SANTYL® Ointment, which includes the protease mixture. In other instances, the composition administered to the wound is not Collagenase SANTYL® Ointment and does not include petrolatum.

In some embodiments, the wound is one that has undergone debridement. Debridement is the medical removal of dead, damaged, or infected tissue to improve the healing potential of the remaining healthy tissue. Removal may be surgical, mechanical, chemical, or autolytic (self-digestion). In some embodiments, the wound is one that is substantially devoid of necrotic tissue. In some embodiments, the debridement or surgical removal occurred just prior to the application of the composition. In some embodiments, the debridement or surgical removal occurred at least, at most, or exactly 1, 5, 10, 20, 30, or 60 minutes (or any derivable range therein) prior to application of the composition. In some embodiments, the debridement or surgical removal occurred at least, at most, or exactly 1, 2, 3, 4, 5, 6, 7, 10, 20, 24, 48, or 72 hours (or any derivable range therein) prior to application of the composition. In some embodiments, the wound is one that is at least, at most, or exactly 60, 70, 80, 85, 90, or 99% (or any derivable range therein) devoid of necrotic tissue. In some embodiments, the wound is at least partially or at least mostly devoid of necrotic tissue. In some embodiments, the wound is one that is entirely devoid of necrotic tissue. In some embodiments, the wound is one that would not benefit from a debridement or surgical removal treatment at the time of application of the composition.

In some embodiments, the wound is a chronic wound. A chronic wound is a wound that does not heal in an orderly set of stages and in a predictable amount of time the way most wounds do; wounds that do not heal within three months are often considered chronic. Examples of chronic wounds are diabetic foot ulcers, venous leg ulcers, arterial leg ulcers, decubitus ulcers, stasis ulcers, dermal ulcers, burns, and pressure ulcers. In some embodiments the wound is a dermal ulcer, a diabetic foot ulcer, venous leg ulcer, peptic ulcer, etc. In some embodiments, the wound is a burn. A burn is a type of injury to flesh or skin caused by heat, electricity, chemicals, friction, or radiation. In some embodiments, the wound is a surgical wound. In some embodiments, the wound is a surgical, hypertrophic, cosmetic, or keloid scar.

In some embodiments, the composition is sterile. In some embodiments, the composition is administered topically. In some embodiments, the composition further comprises petrolatum. In some embodiments, the composition further comprises an antimicrobial agent. In some embodiments, the antimicrobial agent is an antibiotic or an antiseptic. Alternatively, the composition may further comprise one or more components described throughout the disclosure.

The embodiments in the Example section are understood to be embodiments of the invention that are applicable to all aspects of the invention. Also disclosed in the context of the present invention are embodiments 1 to 23. Embodiment 1 is a method for repairing a wound comprising administering a composition comprising a protease mixture comprising collagenases and a neutral protease to the wound in an amount effective for repair of the wound tissue. Embodiment 2 is a method for inducing the proliferative phase of a wound comprising administering a composition comprising a protease mixture comprising collagenases and a neutral protease to the wound in an amount effective for the induction of the proliferative phase in the wound. Embodiment 3 is the method of embodiment 2, wherein the proliferative phase comprises angiogenesis. Embodiment 4 is the method of embodiment 2, wherein the proliferative phase comprises epithelialization. Embodiment 5 is the method of any one of embodiments 1 to 4, wherein the protease mixture is obtained from fermenting *Clostridium histolyticum* and includes collagenase ColG, collagenase ColH, and non-specific neutral protease. Embodiment 6 is the method of any one of embodiments 1 to 5, wherein the protease mixture is the active pharmaceutical ingredient (API) in SANTYL® Ointment. Embodiment 7 is the method of any one of embodiments 1 to 6, wherein the composition is comprised in a wound dressing. Embodiment 8 is the method of embodiment 7, wherein the wound dressing is a patch, wrap, or bandage. Embodiment 9 is the method of any one of embodiments 1 to 6, wherein the composition is comprised in a spray. Embodiment 10 is the method of any one of embodiments 1 to 6, wherein the composition is a liquid, salve, dissolvable gel-forming film, cream, powder, film, or semi-solid. Embodiment 11 is the method of any one of embodiments 1 to 10, wherein the wound is one that has been debrided prior to administration of the composition. Embodiment 12 is the method of any one of embodiments 1 to 11, wherein the wound is substantially devoid of necrotic tissue prior to administration of the composition. Embodiment 13 is the method of any one of embodiments 1 to 12, wherein the wound is a burn. Embodiment 14 is the method of any one of embodiments 1 to 12, wherein the wound is a chronic wound. Embodiment 15 is the method of any one of embodiments 1 to 12, wherein the wound is a non-healing wound. Embodiment 16 is the method of any one of embodiments 1 to 12, wherein the wound is a diabetic foot ulcer, venous leg ulcer, arterial leg ulcer, decubitus ulcer, stasis ulcer, dermal ulcer, pressure ulcer or a peptic ulcer. Embodiment 17 is the method of any one of embodiments 1 to 12, wherein the wound is a surgical, hypertrophic, cosmetic, or keloid scar. Embodiment 18 is the method of any one of embodiments 1 to 17, wherein the composition is sterile. Embodiment 19 is the method of any one of embodiments 1 to 18, wherein the composition is administered topically. Embodiment 20 is the method of any one of embodiments 1 to 19, wherein the composition further comprises petrolatum. Embodiment 21 is the method of any one of embodiments 1 to 20, wherein the composition does not include petrolatum. Embodiment 22 is the method of any one of embodiments 1 to 20, wherein the composition further comprises an antimicrobial agent. Embodiment 23 is the method of embodiment 22, wherein the antimicrobial agent is an antibiotic or an antiseptic.

The phrase "protease mixture" means a mixture that includes collagenase ColG, collagenase ColH, and neutral protease that has also been produced by protease mixture produced by the fermentation of *Clostridium histolyticum*. Collagenase ColG has a molecular weight (MW) of 114 kDa. Collagenase ColH has a MW of 110 kDa. Neutral protease has a MW of 35 kDa. For example, the active ingredient in the SANTYL® Ointment would be included in the definition of "protease mixture." By comparison, collagenase that has been produced from *Clostridium histolyti-*

*cum* and has been purified (e.g., the collagenase in U.S. Pat. No. 5,851,522) would not be included in the definition of "protease mixture." In one non-limiting aspect, the protease mixture can be obtained from fermentation of *Clostridium histolyticum* (ATCC 21000).

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DESCRIPTION OF THE ILLUSTRATIVE EMBODIMENTS

A. Wound Repair Process

Figure 1:
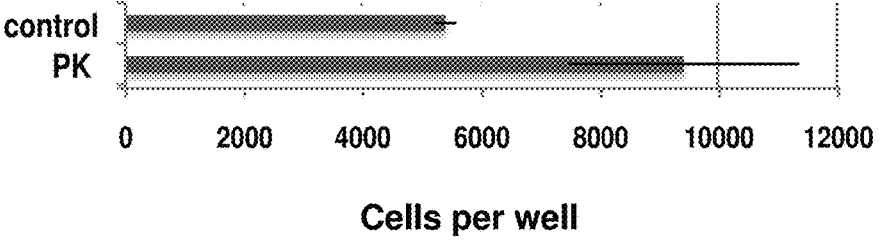
FIG. 1 shows that the active pharmaceutical ingredient from the SANTYL® Ointment ("SANTYL® Collagenase API (called PK collagenase)) stimulates proliferation of adult human keratinocytes. Adult human keratinocytes were plated at low density in multi-well plates and treated with PK every other day. At day 7 post-plating the cells were counted using a coulter counter. Cell proliferation relative to absolute cell number grown is shown.

The wound repair process is subdivided into three phases: (1) inflammation, (2) proliferation and (3) remodeling. The time course of the different cells that appear in the wound during the repairing process has been characterized extensively. For example, neutrophils are predominant during inflammation, whereas fibroblasts are predominant during the proliferative phase. As an initial reaction to a wound, the body mounts an inflammatory response which is characterized by the recruitment of granulocytes, predominantly neutrophils, and cells from the monocyte-macrophage lineage to the site of injury. While neutrophilic inflammation is traditionally regarded as a normal acute response, the continual presence of neutrophils is often associated with delayed wound repair and chronically stalled wounds. In the normal trajectory of wound repair, the proliferative phase, where epithelialization, angiogenesis and provisional matrix formation takes place, is typically initiated after neutrophils have been cleared out by activated macrophages. Therefore, fibroblasts are the predominant cell-type found during the proliferative phase of a healthy, repairing wound.

The methods disclosed herein may be effective in promoting wound repair by inducing the proliferative phase of wound repair. About two or three days after the wound occurs, fibroblasts begin to enter the wound site, marking the onset of the proliferative phase even before the inflammatory phase has ended. The proliferative phase includes multiple aspects. It is contemplated that the compositions described herein can be used in methods for promoting one or more aspects of the proliferative phase described below.

One aspect of the proliferative phase includes angiogenesis. In some embodiments, the method is for inducing angiogenesis in the wound. Angiogenesis, also called neovascularization, is a process that occurs concurrently with fibroblast proliferation when endothelial cells migrate to the area of the wound. Because the activity of fibroblasts and epithelial cells requires oxygen and nutrients, angiogenesis is imperative for other stages in wound healing, like epidermal and fibroblast migration.

A further aspect of the proliferative phase is fibroplasia and granulation tissue formation. Simultaneously with angiogenesis, fibroblasts begin accumulating in the wound site. Fibroblasts begin entering the wound site two to five days after wounding as the inflammatory phase is ending, and their numbers peak at one to two weeks post-wounding. By the end of the first week, fibroblasts are the main cells in the wound. Fibroplasia ends two to four weeks after wounding. In the first two or three days after injury, fibroblasts mainly migrate and proliferate, while later, they are the main cells that lay down the collagen matrix in the wound site. Initially fibroblasts utilize the fibrin cross-linking fibers to migrate across the wound, subsequently adhering to fibronectin. Fibroblasts then deposit ground substance into the wound bed, and later collagen, which they can adhere to for migration. Granulation tissue functions as rudimentary tissue, and begins to appear in the wound already during the inflammatory phase, two to five days post wounding, and continues growing until the wound bed is covered. Granulation tissue consists of new blood vessels, fibroblasts, inflammatory cells, endothelial cells, myofibroblasts, and the components of a new, provisional extracellular matrix (ECM). Later the provisional matrix is replaced with an ECM that more closely resembles that found in non-injured tissue.

A further aspect of the proliferative phase is collagen deposition. Collagen deposition is important because it increases the strength of the wound; before it is laid down, the only thing holding the wound closed is the fibrin-fibronectin clot, which does not provide much resistance to traumatic injury. Also, cells involved in inflammation, angiogenesis, and connective tissue construction attach to, grow and differentiate on the collagen matrix laid down by fibroblasts.

The proliferative phase also encompasses epithelialization. The formation of granulation tissue into an open wound allows the reepithelialization phase to take place, as epithelial cells migrate across the new tissue to form a barrier between the wound and the environment.

A further aspect of the proliferative phase is contraction. Contraction commences approximately a week after wounding, when fibroblasts have differentiated into myofibroblasts. In full thickness wounds, contraction peaks at 5 to 15 days post wounding. Contraction can last for several weeks and continues even after the wound is completely reepithelialized. Contraction usually does not occur symmetrically; rather most wounds have an 'axis of contraction' which allows for greater organization and alignment of cells with collagen.

B. Protease Mixture

The protease mixture of the present invention is produced by fermenting *Clostridium histolyticum* and includes collagenases and a neutral protease. In particular, the mixture includes two collagenases, ColG (MW about 114 kDa) and ColH (MW about 110 kDa), and a non-specific neutral protease (a metalloproteinase with a MW about 35 kDa). It has very limited amount of clostripain (cysteine protease). The activity of clostripain in the mixture is not detected by casein zymogram. In one instance, the mixture includes 1 wt. % to 10 wt. % or 1 wt. % to 5 wt. % or 2 wt. % to 4 wt. % or about 3 wt. % of a neutral protease (molecule weight (MW) about 35 kDa), which is a non-specific metalloprotease. In other instances, the protease mixture of the present invention does not include or contains limited amounts (e.g., less than 1 wt. % or less than 0.5 wt. % or less than 0.1 wt. % or less than 0.01 wt. %) of clostripain. A non-limiting example of such a protease mixture is the active ingredient used in the aforementioned SANTYL® Ointment (called PK collagenase), which is an FDA-approved prescription medicine that debrides wounds to prepare the wound bed for further administration of wound healing agents. The Ointment is a sterile composition that contains 250 collagenase units per gram of white petrolatum USP.

In particular instances of the present invention, the protease mixture can be applied to a wound after the wound has already been debrided, such as with the SANTYL® Ointment. By way of example, the SANTYL® Ointment can be first applied to a wound to debride necrotic tissue. Subsequently, a protease mixture of the present invention can then be applied. Still further, the Ointment can be first removed from the wound followed by application of the protease mixture. Alternatively, the Ointment can be first applied to debride the wound and then a protease mixture of the present invention can be subsequently applied.

C. Pharmaceutical Compositions

In addition to the protease mixture, the compositions of the present invention can include additional non-active components such as carriers or diluents which will not interfere with the intended purpose of the composition. The compositions may, for example, take the form of solutions, suspensions, instillations, sprays, salves, creams, gels, foams, ointments, emulsions, lotions, paints, sustained release formulations, dissolvable gel-forming films, or powders, and typically contain about 0.01% to about 1% of active ingredient(s), about 1%-50% or active ingredient(s), about 2%-60% of active ingredient(s), about 2%-70% of active ingredient(s), or up to about 90%) of active ingredient (s). Other suitable formulations include poloxamer gel-based formulations, carboxymethylcellulose (CMC)-based formulations, hydroxylethylcellulose (HEC)-based formulations, hydroxypropycellulose (HPC)-based formulations, and hyroxypropylmethylcellulose (HPMC)-based formulations. Other useful formulations include slow or delayed release preparations. In some specific embodiments, the composition is formulated as an ointment.

Gels or jellies may be produced using a suitable gelling agent including, but not limited to, gelatin, tragacanth, or a cellulose derivative and may include glycerol as a humectant, emollient, and preservative. Ointments are semi-solid preparations that consist of the active ingredient incorporated into a fatty, waxy, or synthetic base. Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH. In some embodiments, the compositions comprise petrolatum. In some embodiments, the compositions comprise white petrolatum.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Suitable carriers and diluents include isotonic saline solutions, for example phosphate-buffered saline. Suitable diluents and excipients also include, for example, water, saline, dextrose, glycerol, or the like, and combinations thereof. In addition, if desired substances such as wetting or emulsifying agents, stabilizing or pH buffering agents may also be present.

The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, and amino acid copolymers.

Pharmaceutically acceptable salts can also be present, e.g., mineral acid salts such as hydrochlorides, hydrobromides, phosphates, sulfates, and the like; and the salts of organic acids such as acetates, propionates, malonates, benzoates, and the like.

Suitable carrier materials include any carrier or vehicle commonly used as a base for creams, lotions, sprays, foams, gels, emulsions, lotions or paints for topical administration. Examples include emulsifying agents, inert carriers including hydrocarbon bases, emulsifying bases, non-toxic solvents or water-soluble bases. Examples include poloxamers, petrolatum, white petrolatum, HPMC, CMC and other cellulose-based ingredients, lanolin, hard paraffin, liquid paraffin, soft yellow paraffin or soft white paraffin, white beeswax, yellow beeswax, cetostearyl alcohol, cetyl alcohol, dimethicones, emulsifying waxes, isopropyl myristate, microcrystalline wax, oleyl alcohol and stearyl alcohol. In some embodiments, the compositions comprise petrolatum. In some embodiments, the compositions comprise white petrolatum.

Auxiliary agents such as casein, gelatin, albumin, glue, sodium alginate, carboxymethylcellulose, methylcellulose, hydroxyethylcellulose or polyvinyl alcohol may also be included in the compositions described herein.

D. Additional Therapeutic Components

The compositions described herein may also include additional therapeutic components that are known to treat skin conditions and/or wounds. Such therapeutic components include antimicrobials such as, for example, antiseptics and antibiotics.

Antiseptics are disinfectants that can be used on intact skin and some open wounds to kill or inhibit microorganisms. They often have multiple microbial targets, a broad antimicrobial spectrum, and residual anti-infective activity but are often toxic to host tissues (e.g., fibroblasts, keratinocytes, and possibly leukocytes). Commonly used antiseptics include hydrogen peroxide, which has limited bactericidal and debriding activity; and chlorhexidine, which has long-acting activity against a wide range of both gram-negative and gram-positive bacteria.

Antibiotics are chemicals produced either naturally (by a microorganism) or synthetically that in dilute solution inhibit or kill other microorganisms. They usually act on one specific cell target, have a narrower spectrum of activity, are relatively nontoxic, and are more susceptible to losing their effectiveness to bacterial resistance. The first topical antibiotics were derived from agents developed for systemic use (i.e., sulfonamides in the mid-1930s), followed in the next decade by topical penicillins, bacitracin, gramicidin, aminoglycosides (including neomycin), polymixin, tetracyclines, and cholor-am-phen-i-col. Agents introduced later include fusidic acid, clindamycin, mupirocin and retapamulin. Antibiotics that may be used in the compositions described in the disclosure include bacitracin, fisidic acid, gentamicin, mafenide acetate, mupirocin and mupirocin calcium, neomycin sulfate, nitrofurazone, polymixin B, retapumulin, and sulfacetamide.

The compositions described herein may also comprise additional agents that reduce skin inflammation such as, for example, antihistamines, corticosteroids (e.g. hydrocortisone or clobetasol propionate), and immunosuppressants (e.g. pimecrolimus and tacrolimus).

The compositions described herein may also be combined with other treatments known in the art to promote wound repair.

E. Doses

The composition may be present in a vehicle or administered in any effective amount. In some embodiments, the composition is formulated as 250 units (Unit definition: The potency assay of collagenase in SANTYL® Ointment is based on the digestion of undenatured collagen from bovine Achilles tendon at pH 7.2 and 37° C. for 24 hours. The number of peptide bonds cleaved is measured by reaction with ninhydrin. Amino groups released from the collagen by a trypsin digestion control are subtracted. One net collagenase unit will hydrolyze undenatured collagen to produce ninhydrin reactive material equivalent to 1.09 nmol of leucine equivalents per minute.) of collagenase per gram of composition. In some embodiments composition may be formulated as 100, 150, 200, 250, 300, 350, 400, or 500 units (or any derivable range therein) of collagenase per gram of composition. In some embodiments, 0.5, 1, 2, 3, 4, 5, or 7 (or any derivable range therein) of composition is applied to the skin or wound. In some embodiments, the composition is applied every 2, 6, or 8 hours or every 1, 2, 4, 7, or 10 days (or any derivable range thereof).

In some embodiments, the composition is applied to a wound after a wound has been debrided. In some embodiments, the wound is substantially free of necrotic tissue. In some embodiments, the wound is entirely free of necrotic tissue. Methods for determining whether there is necrotic tissue remaining in the wound are known in the art. For example, necrotic tissue is easily visualized by the trained healthcare professional, and whether a wound is devoid of necrotic tissue can be visually determined.

F. Wound Dressings

In some aspects, the compositions described herein are provided in the form of a wound dressing. The wound dressing may contain one or more agents specific to a desired biomarker. The term "wound dressing" used herein is taken to include any medically or pharmaceutically acceptable wound covering or support matrix. Examples of suitable wound dressing materials include, but are not limited to, a) films, including those of a semipermeable or a semi-occlusive nature such as polyurethane copolymers, polyurethane film, acrylamides, acrylates, paraffin, polysaccharides, cellophane and lanolin; b) hydrocolloids including carboxymethylcellulose protein constituents of gelatin, pectin, and complex polysaccharides including Acacia gum, guar gum and karaya, which may be utilized in the form of a flexible foam, formulated in polyurethane, or formulated as an adhesive mass such as polyisobutylene; c) polymers such as agar, starch or propylene glycol, which typically contain about 80% to about 90% water and are conventionally formulated as sheets, powders, pastes and gels in conjunction with cross-linked polymers such as polyethylene oxide, polyvinyl pyrollidone, acrylamide, propylene glycol; d) foams such as polysaccharide which consist of a hydrophilic open-celled contact surface and hydrophobic closed-cell polyurethane; e) impregnates including pine mesh gauze, paraffin and lanolin-coated gauze, polyethylene glycol-coated gauze, knitted viscose, rayon, and polyester; and f) cellulose-like polysaccharide such as alginates, including calcium alginate, which may be formulated as non-woven composites of fibers or spun into woven composites.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Wound Repair by *Clostridium histolyticum* Collagenase

Figure 2:
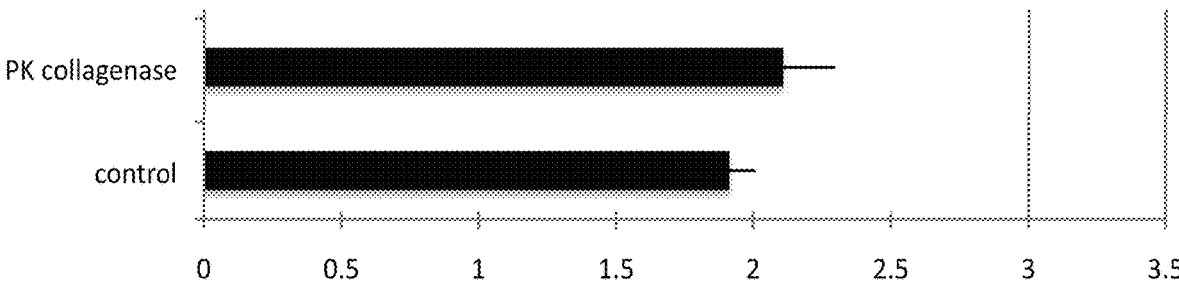
FIG. 2 demonstrates that SANTYL® Collagenase API (called PK collagenase) stimulate wound healing in mice. Wounds were created and treated as described in Example 1 and scored in a blind manner according to the grading described in the Example. * indicates statistical significance of findings (p<0.05).
Figure 3:
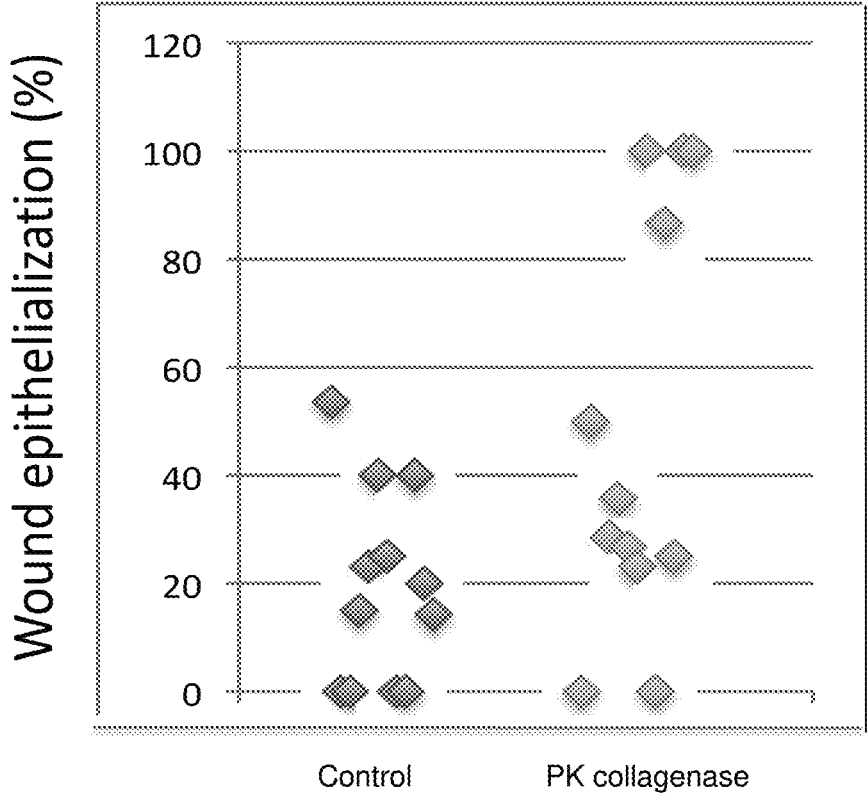
FIG. 3 shows that SANTYL® Collagenase API (called PK collagenase) stimulates wound epithelialization in mice. Wounds were created and treated as described in FIG. 1. Wound epithelialization was measured at day 6 post wounding.

To test the wound-healing effects of collagenase, the Collagenase active pharmaceutical ingredient (API) that is used in SANTYL® Ointment (called PK collagenase) was tested for its ability to promote adult human keratinocyte proliferation. As shown in FIG. 1, the SANTYL® collagenase API (identified as PK) promoted adult human keratinocyte proliferation. It was further found that the SANTYL® collagenase API stimulated wound healing and epithelization in mice. For this experiment, established models of injury and repair, such as two-dimensional and three-dimensional injury/repair models, were used. As the inventors and others have previously demonstrated, patent microvascular endothelial lined 'tubes' can be produced in vitro when cells are either plated upon or are embedded within growth factor-reduced Matrigel. For these studies, animals are first treated with cyclophosphamide to induce neutropenia, and then full thickness excisional wounding of the cutaneous tissues located over the cranium of mice was performed. While only one 8 mm diameter full thickness excisional wound can be made/mouse, the means by which healing occurs is closely aligned with human cutaneous wound healing, i.e. via migration and proliferation vs. contraction (as is the case on the rodents' flanks). Following cyclophosphamide treatment, animals are injured and then wounds treated/covered. Test entities are coded so that the nature of the experiment is blinded to the investigator; and, each specimen is evaluated and scored blindly, prior to unmasking the experimental code. As shown in FIGS. 2-3, the SANTYL® collagenase API (identified as PK collagenase) stimulated wound healing (FIG. 2) and wound epithelialization (FIG. 3) in vivo. The tables below show the wound scoring system (Table 1) and further describe the wound healing data (Table 2).

TABLE 1

| Wound Scoring System | |
| --- | --- |
| Score | Description |
| 1 | No epithelialization, no granulation tissue |
| 2 | No epithelialization, granulation tissue poorly formed |
| 3 | Complete epithelialization, granulation tissue poorly formed |
| 4 | Complete epithelialization, well-defined granulation tissue |

TABLE 2

| Wound Healing Data | | | |
| --- | --- | --- | --- |
| Treatment | N | Score | Significance |
| Control | 17 | 1.9 | NA |
| PK collagenase (SANTYL ® API) | 13 | 2.1 | P = 0.0089 |

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method for treating a wound, the method comprising administering a composition comprising a protease mixture comprising collagenases and a neutral protease to the wound in an amount effective for treating the wound, wherein the protease mixture is obtained from fermenting *Clostridium histolyticum* and comprises collagenase ColG, collagenase ColH, and non-specific neutral protease, wherein the wound is not in need of debridement, and wherein the protease mixture is administered to the wound prior to granulation tissue formation in the wound and promotes granulation tissue formation in the wound.

2. The method of claim 1, wherein the wound is substantially devoid of necrotic tissue.

3. The method of claim 1, wherein the wound is entirely devoid of necrotic tissue.

4. The method of claim 1, wherein the wound was debrided prior to administration of the composition.

5. The method of claim 4, wherein the wound was debrided with an enzymatic debriding agent.

6. The method of claim 5, wherein the enzymatic debriding agent comprises a protease mixture obtained from fermenting *Clostridium histolyticum* and comprises collagenase ColG, collagenase ColH, and non-specific neutral protease.

7. The method of claim 1, wherein administration of the composition to the wound induces fibroblast proliferation, induces angiogenesis, epithelialization, or a combination thereof to promote repair of the wound.

8. The method of claim 1, wherein the composition is comprised in a wound dressing.

9. The method of claim 8, wherein the wound dressing is a patch, wrap, or bandage.

10. The method of claim 1, wherein the composition is a spray, liquid, salve, dissolvable gel-forming film, cream, powder, film, or semi-solid.

11. The method of claim 1, wherein the composition is sterile.

12. The method of claim 1, wherein the composition is administered topically.

13. The method of claim 1, wherein the composition consists of collagenase ColG, collagenase ColH, non-specific neutral protease, and petrolatum.

14. The method of claim 1, wherein the composition does not include petrolatum.

15. The method of claim 1, wherein the composition further comprises an antimicrobial agent selected from an antibiotic or an antiseptic.

16. The method of claim 1, wherein the wound is a burn.

17. The method of claim 1, wherein the wound is a chronic wound or a non-healing wound.

18. The method of claim 1, wherein the wound is a diabetic foot ulcer, venous leg ulcer, arterial leg ulcer, decubitus ulcer, stasis ulcer, dermal ulcer, pressure ulcer or a peptic ulcer.

19. The method of claim 1, wherein the wound is a surgical, hypertrophic, cosmetic, or keloid scar.

20. The method of claim 1, wherein the wound is unhealed and in need of repair.

* * * * *